United States Patent [19]

Powers et al.

[11] Patent Number: 5,415,675
[45] Date of Patent: May 16, 1995

[54] FRAGRANCED RETURN AIR FILTERS

[76] Inventors: Betty J. Powers, P.O. Box 13941, New Bern, N.C. 28560; George Spector, 233 Broadway Rm 702, New York, N.Y. 10279

[21] Appl. No.: 151,140

[22] Filed: Nov. 12, 1993

[51] Int. Cl.$^6$ .............................................. B01D 46/00
[52] U.S. Cl. .................................... 55/279; 55/518; 55/524; 422/4; 422/123
[58] Field of Search ................. 55/279, 495, 516, 518, 55/524, DIG. 31, DIG. 35; 422/4, 5, 120, 123

[56] References Cited

U.S. PATENT DOCUMENTS

| | | | |
|---|---|---|---|
| 3,902,877 | 9/1975 | Swaim | 55/279 |
| 4,028,073 | 6/1977 | Swaim | 55/279 |
| 4,306,892 | 12/1981 | Atalla et al. | 422/123 |
| 4,477,272 | 10/1984 | Hollis et al. | 55/279 |
| 4,563,333 | 1/1986 | Frigon | 55/279 |
| 4,604,114 | 8/1986 | Ward | 55/279 |
| 4,875,912 | 10/1989 | Fulmer | 55/279 |
| 5,087,273 | 2/1992 | Ward | 422/5 |

FOREIGN PATENT DOCUMENTS

| | | | |
|---|---|---|---|
| 62907 | 1/1914 | German Dem. Rep. | 55/279 |
| 501309 | 11/1954 | Italy | 55/279 |

Primary Examiner—Charles S. Bushey

[57] ABSTRACT

A fragrance return air filter is provided with an air filter for removing impurities from air being forced through the air filter and at least one fragrant impregnated sponge strip mounted on the air filter, so that a fresh clean scent can mix with the filtered air passing through the sponge strip and the air filter.

1 Claim, 1 Drawing Sheet

FRAGRANCED RETURN AIR FILTERS

BACKGROUND OF THE INVENTION

The instant invention relates generally to air fresheners and more specifically it relates to a fragrance return air filter which provides a fresh clean scent into the filtered air passing through. There are available various conventional air fresheners which do not provide the novel improvements of the invention herein disclosed.

SUMMARY OF THE INVENTION

A primary object of the present invention is to provide a fragrance return air filter that will overcome the shortcomings of the prior art devices.

Another object is to provide a fragrance return air filter in which fragrant impregnated sponge strips are mounted on an air filter, so that a fresh clean scent can mix with the filtered air passing through.

An additional object is to provide a fragrance return air filter in which the fragrant impregnated sponge strips include hook members that are engagable with the fibrous filtering material of the air filter to be better gripped thereto.

A further object is to provide a fragrance return air filter that is simple and easy to use.

A still further object is to provide a fragrance return air filter that is economical in cost to manufacture.

Further objects of the invention will appear as the description proceeds.

To the accomplishment of the above and related objects, this invention may be embodied in the form illustrated in the accompanying drawings, attention being called to the fact, however, that the drawings are illustrative only, and that changes may be made in the specific construction illustrated and described within the scope of the appended claims.

BRIEF DESCRIPTION OF THE DRAWING FIGURES

DETAILED DESCRIPTION OF THE PREFERRED EMBODIMENTS

Figure 1:
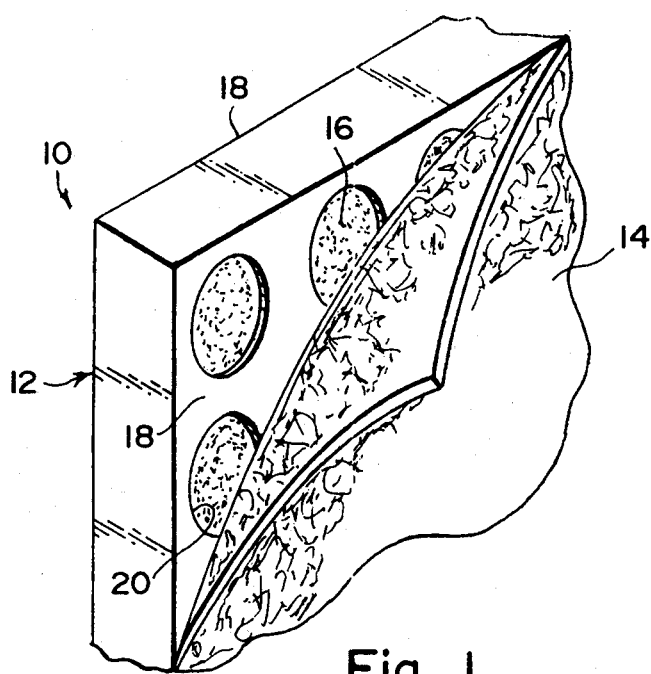
FIG. 1 is a perspective view of a corner of the instant invention with the fragrant impregnated sponge strip folded back.
Figure 2:
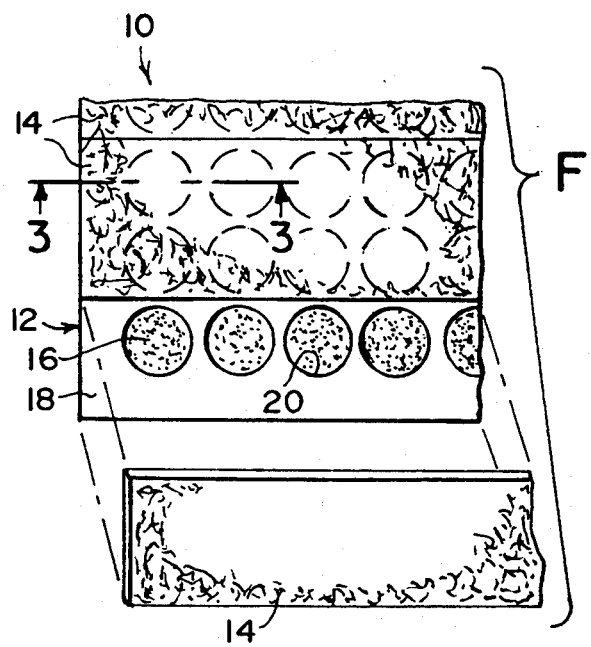
FIG. 2 is a front perspective view of the corner of the air filter showing one of the sponge strips exploded therefrom.

Turning now descriptively to the drawings, in which similar reference characters denote similar elements throughout the several views, FIGS. 1 through 5 illustrate a fragrance return air filter 10 which consists of an air filter 12 for removing impurities from air being forced through the air filter 12. At least one fragment impregnated sponge strip 14 is mounted on the air filter 12 so that a fresh clean scent can mix with the filtered air passing through the sponge strip 14 and the air filter 12.

The air filter 12 includes a fibrous filtering material pad 16 and a pair of backing members 18. Each backing member 18 has a plurality of apertures 20, whereby the backing members 18 sandwich the fibrous filtering material pad 16 therebetween.

Figure 3:
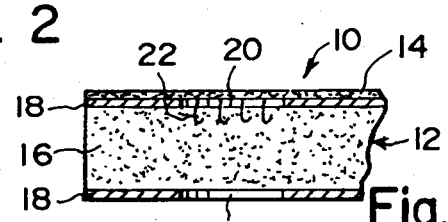
FIG. 3 is a cross sectional view taken along line 3—3 in FIG. 2, showing a modified sponge strip with hook members engagable within the fibrous filtering material in the air filter.
Figure 4:
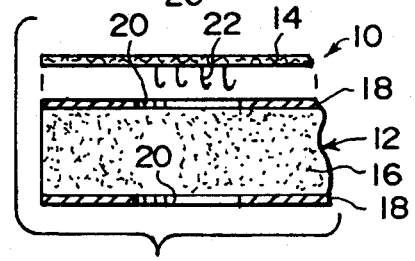
FIG. 4 is a cross sectional view similar to FIG. 3, showing the sponge strip exploded therefrom.

As shown in FIGS. 3 and 4, the at least one fragrant impregnated sponge strip 14 further includes a plurality of hook members 22 extending from one side thereof, aligned with the apertures 20, so that the hook members 22 pass through the apertures 20 and engage with the fibrous filtering material pad 16, to better secure the sponge strip 14 to the air filter 12.

Figure 5:
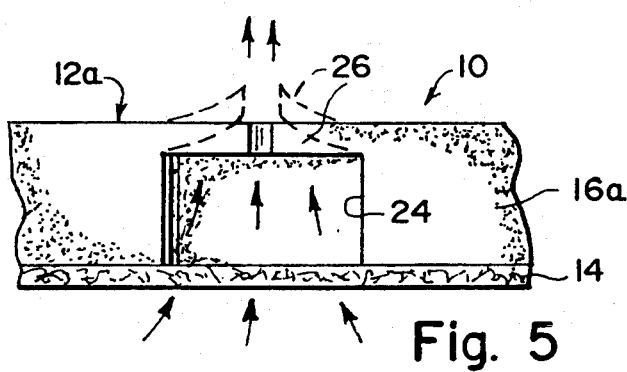
FIG. 5 is a cross sectional view of another modification showing the fibrous filtering material of the air filter having a hole therein with an air valve flap in the hole which will open when air is forced through the sponge strip and through the fibrous filtering material of the air filter.

FIG. 5 shows a portion of a modified air filter 12a that includes a fibrous filtering material pad 16a having a plurality of holes 24 therein. A plurality of air valve flaps 26 are also provided, integral with the pad 16a adjacent each of the holes 24. Each air valve flap 26 will open when air is forced through the at least one fragrant impregnated sponge strip 14 and through the fibrous filtering material pad 16a of the air filter 12a.

While certain novel features of this invention have been shown and described and are pointed out in the annexed claims, it will be understood that various omissions, substitutions and changes in the forms and details of the device illustrated and in its operation can be made by those skilled in the art without departing from the spirit of the invention.

What is claimed is:

1. A fragrance return air filter which comprises:
   a) an air filter for removing impurities from air being forced through said air filter;
   b) at least one fragrant impregnated sponge strip mounted on said air filter so that a fresh clean scent mixes with the filtered air passing through said sponge strip and said air filter; wherein said air filter includes:
   c) a fibrous filtering material pad;
   d) a pair of backing members, each having a plurality of apertures, whereby said backing members sandwich said fibrous filtering material pad therebetween; wherein said at least one fragrant impregnated sponge strip further includes a plurality of hook member sets extending from an inner side thereof each said set aligned with said apertures, so that each of said hook members pass through said apertures and include an inner U-shaped portion which engages with said fibrous filtering material pad to better secure said sponge strip to said air filter.

* * * * *